United States Patent
Knotts

(10) Patent No.: US 9,795,386 B2
(45) Date of Patent: Oct. 24, 2017

(54) MULTIPLE BAND ENDOSCOPIC LIGATION DEVICE

(71) Applicant: EndoChoice, Inc., Alpharetta, GA (US)

(72) Inventor: David Joseph Knotts, Canton, GA (US)

(73) Assignee: Endochoice, Inc., Alpharetta, GA (US)

( * ) Notice: Subject to any disclaimer, the term of this patent is extended or adjusted under 35 U.S.C. 154(b) by 0 days.

(21) Appl. No.: 15/194,121

(22) Filed: Jun. 27, 2016

(65) Prior Publication Data

US 2016/0374688 A1    Dec. 29, 2016

Related U.S. Application Data

(63) Continuation of application No. 13/680,646, filed on Nov. 19, 2012, now Pat. No. 9,402,631.

(51) Int. Cl.
*A61B 17/12*    (2006.01)
*A61B 17/00*    (2006.01)

(52) U.S. Cl.
CPC .. *A61B 17/12013* (2013.01); *A61B 17/00234* (2013.01); *A61B 2017/00296* (2013.01); *A61B 2017/12018* (2013.01)

(58) Field of Classification Search
CPC .... A61B 17/12013; A61B 2017/12018; A61B 2017/00296; A61B 17/12; A61B 17/12009; A61F 6/202; A61F 6/204
(Continued)

(56) References Cited

U.S. PATENT DOCUMENTS 5,320,630 A    6/1994 Ahmed
5,398,844 A    3/1995 Zaslavsky
(Continued)

FOREIGN PATENT DOCUMENTS

WO    9716120    5/1997
WO    0245595    6/2002
WO    2006119762 A1    11/2006

OTHER PUBLICATIONS

Office Action dated Feb. 11, 2015 for U.S. Appl. No. 13/680,646.
(Continued)

*Primary Examiner* — Christopher L Templeton
*Assistant Examiner* — George J Ulsh
(74) *Attorney, Agent, or Firm* — Bookoff McAndrews, PLLC

(57) ABSTRACT

A multiple band endoscopic ligation device comprises a single pull string and a plurality of beads positioned on said pull string and between each successive band. The device is configured to be coupled to the distal end of an endoscope and is used to deploy multiple elastic bands around target tissues to be ligated. The device includes a tapered cylindrical body about which a plurality of elastic bands are stretched and positioned. The pull string includes multiple sets of two beads fixed to the string wherein one bead is placed directly behind and in contact with the other. The string is wrapped around the device's body and under each band such that at least one pair of beads is positioned between the elastic bands and one pair of beads is positioned proximally to the most proximal band. As the string is pulled, the beads push the bands sequentially off the distal end of the device and around a tissue to be ligated. The use of two adjacent beads on the string to push off each band ensures that the bands will not slip over the beads, thereby preventing a misfire.

18 Claims, 4 Drawing Sheets

(58) Field of Classification Search
USPC ..................................................... 606/140
See application file for complete search history.

(56) References Cited

U.S. PATENT DOCUMENTS

| | | | |
|---|---|---|---|
| 5,423,834 A | 6/1995 | Ahmed |
| 5,462,559 A | 10/1995 | Ahmed |
| 5,788,715 A | 8/1998 | Watson |
| 6,007,551 A | 12/1999 | Peifer |
| 6,051,003 A | 4/2000 | Chu |
| 6,059,798 A | 5/2000 | Tolkoff |
| 6,066,145 A | 5/2000 | Wurster |
| 6,149,659 A | 11/2000 | Ahmed |
| 6,235,040 B1 | 5/2001 | Chu |
| 6,565,578 B1 | 5/2003 | Peifer |
| 6,676,672 B2 | 1/2004 | Chu |
| 6,730,101 B1 | 5/2004 | Peifer |
| 6,893,393 B2 | 5/2005 | Carrillo |
| 6,929,603 B2 | 8/2005 | Durell |
| 6,974,466 B2 | 12/2005 | Ahmed |
| 7,150,752 B2 | 12/2006 | Suzuki |
| 7,220,227 B2 | 5/2007 | Sasaki |
| 2002/0072757 A1 | 6/2002 | Ahmed |
| 2003/0233043 A1 | 12/2003 | Windheuser |
| 2004/0006256 A1 | 1/2004 | Suzuki |
| 2006/0135846 A1 | 6/2006 | Hunt |
| 2006/0259041 A1 | 11/2006 | Hoffman |
| 2007/0265493 A1 | 11/2007 | Zirps |
| 2008/0015613 A1 | 1/2008 | Saeed |
| 2008/0091218 A1 | 4/2008 | Richardson |
| 2009/0131748 A1 | 5/2009 | Chami |
| 2013/0274766 A1 | 10/2013 | Isaacson |

OTHER PUBLICATIONS

Office Action dated Jun. 15, 2015 for U.S. Appl. No. 13/680,646.
Notice of Allowance dated Mar. 29, 2016 for U.S. Appl. No. 13/680,646.
Corrected Notice of Allowance dated Apr. 13, 2016 for U.S. Appl. No. 13/680,646.

MULTIPLE BAND ENDOSCOPIC LIGATION DEVICE

CROSS-REFERENCE

The present application is a continuation application of U.S. patent application Ser. No. 13/680,646, entitled "Multiple Band Endoscopic Ligation Device" and filed on Nov. 19, 2012.

FIELD

The present specification relates generally to the ligation of internal body tissues. More particularly, the present specification relates to a device for deploying multiple elastic ligating bands around target internal body tissues.

BACKGROUND

Ligation, as it relates to the present specification, is a medical procedure used to remove unwanted anatomical structures from the human body. Elastic or rubber band ligation involves the placement of a constricting band about the unwanted anatomical structures, such as a blood vessel or the base or pedicle of a lesion, to occlude distal blood supply. After the loss of blood supply, the lesion slowly dies, sloughs off, and is passed from the body. Elastic ligation is used in the treatment of conditions such as internal hemorrhoids and mucous colitis.

Typical ligation procedures are performed using a ligating device affixed to the distal end of an endoscope. The ligating device includes one or more elastic bands positioned on its distal end. During the procedure, an elastic band that has been stretched outwardly beyond its relaxed, loop configuration is placed around the proximal portion of an outdrawn target tissue. The band is released and thereafter naturally constricts back to its non-stretched configuration, thereby putting pressure on the target tissue and cutting off blood supply to the distal portions.

U.S. Pat. No. 6,007,551, assigned to Dabegran Technologies, Inc. and Cook Medical Technologies LLC, discloses "An endoscopic ligation apparatus for use with a flexible endoscope having a plurality of channels therethrough including a working channel opening at an auxiliary port, said apparatus comprising: a hollow barrel defining an outer surface and a hollow interior therethrough, and including a distal end and a proximal end; means for mounting said proximal end of said barrel to the insertion end of the flexible endoscope; at least one elastic ligating band removably mounted on said outer surface of said barrel; and a trip wire configured to extend through the working channel of the endoscope and including; a proximal end and a distal end, and a length between said ends sufficient for said distal end to extend beyond the insertion end of the endoscope while the proximal end extends from the auxiliary port; a plurality of strands at said distal end, each of said strands extending through said hollow interior of said barrel beyond said distal end of said barrel and overlaying said outer surface of said barrel underneath said at least one ligating band; and each of said plurality of strands including a least one bead attached thereto and situated adjacent said at least one ligating band between said band and said proximal end of said barrel, whereby tension applied to said proximal end of said trip wire pulls each of said plurality of strands toward said distal end of said barrel such that said bead on each of said strands engage said at least one ligating band to dislodge said band from said barrel, wherein said trip wire includes a bead attached thereto adjacent said proximal end."

U.S. Pat. No. 6,676,672, assigned to SciMed Life Systems, Inc., discloses "A ligating band dispenser, comprising: a support surface having a channel extending substantially therethrough, the support surface having an outer surface; and a plurality of ligating bands supported on the outer face of the support surface; a pull line extending through the channel and generally circumferentially along the outer surface of the support surface, the pull line having a plurality of knots formed thereon, each of the plurality of knots having a diameter greater than a diameter of the pull line, each of the plurality of knots being retained proximally of a corresponding one of the plurality of ligating bands, wherein the pull line loops around a selected one of the plurality of ligating bands."

While current ligation devices have proven to be effective in removing unwanted tissues, they are not without their drawbacks. For example, ligation devices that employ more than one pull line or multiple strands are more difficult to manufacture and use. The presence of multiple wires can also obscure vision when using the device. In addition, current multi-band ligation devices often encounter problems with deploying all of the bands. Specifically, the bands loaded more proximally on the device, and therefore slated to be deployed last, often misfire. When the band is stretched to the diameter of the device, the geometry of the band becomes more compliant, allowing the band to jump over the bead or knot as the line is pulled and resulting in the misfire. Misfired bands remain on the device resulting in unsuccessful treatment of the lesion.

Therefore, what is needed is a multi-band ligation device that has an improved, more reliable deployment mechanism, particularly for the proximal bands.

SUMMARY

The present specification is directed toward an endoscopic ligation device for use with an endoscope having a proximal end and a distal end and a first tubular channel therebetween, said device comprising: a cylindrical body having a smooth external surface, a diameter, a proximal end and a distal end and a second tubular channel therebetween wherein said proximal end of said cylindrical body is configured to couple to said distal end of said endoscope such that said first tubular channel is in fluid communication with said second tubular channel; a plurality of elastic bands having a most proximal elastic band and a most distal elastic band, wherein each band is stretched beyond its relaxed diameter and positioned around said external surface of said cylindrical body and further wherein said relaxed diameter of each band is less than the diameter of said cylindrical body; and, a single pull line having a plurality of bead sets fixed along its length, wherein each of said bead sets comprises at least two beads positioned one directly behind and in contact with the other, further wherein said pull line has a first end and a second end and is wrapped around said external surface of said cylindrical body multiple times and under said elastic bands such that at least one set of beads is positioned between said elastic bands.

In one embodiment, the first end of said pull line comprises a bead set and is positioned proximal to said most proximal elastic band and said second end of said pull line passes over the distal end of said cylindrical body, into said second tubular channel, through said first tubular channel, and to a retracting assembly at the proximal end of said endoscope. In one embodiment, the retracting assembly comprises any one of a spooling mechanism, a linear mechanism, and a cam mechanism.

In one embodiment, the cylindrical body has a first diameter at said proximal end and a second diameter at said distal end wherein said first diameter is greater than said second diameter and wherein said first and second diameters are greater than said relaxed diameter of said elastic bands.

In one embodiment, the beads are made of any one of glass, hard plastic, and ceramic. In one embodiment, the beads measure between 0.040 and 0.060 inches in height and have a thickness of between 0.050 and 0.090 inches. In one embodiment, the beads are fixed to said pull line with glue. In one embodiment, each of said plurality of elastic bands has a height of approximately 0.040 inches. In one embodiment, said plurality of elastic bands equals seven.

In one embodiment, the pull line passes one quarter length around the outer surface of said cylindrical body between each set of bands.

The present specification is also directed toward an endoscopic ligation device for use with an endoscope having a proximal end and a distal end and a first tubular channel therebetween, said device comprising: a cylindrical body having a smooth external surface, a diameter, a proximal end and a distal end and a second tubular channel therebetween, wherein said proximal end of said cylindrical body is configured to couple to said distal end of said endoscope such that said first tubular channel is in fluid communication with said second tubular channel; a plurality of elastic bands, each band stretched beyond its relaxed diameter and positioned around said external surface of said cylindrical body wherein said relaxed diameter of each band is less than the external diameter of said cylindrical body; and, a single pull line having a plurality of large beads fixed along its length, wherein said pull line has a first end and a second end and is wrapped around said external surface of said cylindrical body multiple times and under said elastic bands such that at least one bead, having a height within the range of 0.040 to 0.060 inches and a thickness within the range of 0.070 to 0.140 inches, is positioned between said elastic bands.

In one embodiment, the first end of said pull line comprises a single bead and is positioned proximal to said most proximal elastic band and said second end of said pull line passes over the distal end of said cylindrical body, into said second tubular channel, through said first tubular channel, and to a retracting assembly at the proximal end of said endoscope. In one embodiment, the retracting assembly comprises any one of a spooling mechanism, a linear mechanism, and a cam mechanism.

In one embodiment, the cylindrical body has a first diameter at said proximal end and a second diameter at said distal end wherein said first diameter is greater than said second diameter and wherein said first and second diameters are greater than said relaxed diameter of said elastic bands.

In one embodiment, the beads are made of any one of glass, hard plastic, and ceramic. In one embodiment, the beads are fixed to said pull line with glue. In one embodiment, each of said plurality of elastic bands has a height of 0.040 inches. In one embodiment, the plurality of elastic bands equals seven.

The present specification is also directed toward a method for ligating internal body tissues, said method comprising the steps of: providing an endoscopic ligation device for use with an endoscope having a proximal end and a distal end and a first tubular channel therebetween, said device comprising: a cylindrical body having a smooth external surface, a diameter, a proximal end and a distal end and a second tubular channel therebetween wherein said proximal end of said cylindrical body is configured to couple to said distal end of said endoscope such that said first tubular channel is in fluid communication with said second tubular channel; a plurality of elastic bands having a most proximal elastic band and a most distal elastic band, wherein each band stretched beyond its relaxed diameter and positioned around said external surface of said cylindrical body and further wherein said relaxed diameter of each band is less than the external diameter of said cylindrical body; and, a single pull line having a plurality of bead sets fixed along its length, wherein each of said bead sets comprises at least two beads positioned one directly behind and in contact with the other, further wherein said pull line has a first end and a second end and is wrapped around said external surface of said cylindrical body multiple times and under said elastic bands such that at least one set of beads is positioned between said elastic bands; wherein said first end of said pull line comprises a bead set and is positioned proximal to said most proximal elastic band and said second end of said pull line passes over the distal end of said cylindrical body, into said second tubular channel, through said first tubular channel, and to a retracting assembly at the proximal end of said endoscope; attaching said proximal end of said device to said distal end of said endoscope; inserting said distal end of said endoscope with attached device into a patient; maneuvering said distal end of said endoscope with attached device to a target tissue; placing said distal end of said device over said target tissue; applying suction to said proximal end of said endoscope to draw a portion of said target tissue into said device; and, actuating said retracting assembly to apply tension to said pull string to push the most distal bead set against the most distal elastic band, deploying said most distal elastic band off the distal end of said device and around said target tissue.

The present specification is also directed toward a method for ligating internal body tissues, said method comprising the steps of: providing an endoscopic ligation device for use with an endoscope having a proximal end and a distal end and a first tubular channel therebetween, said device comprising: a cylindrical body having a smooth external surface, a diameter, a proximal end and a distal end and a second tubular channel therebetween wherein said proximal end of said cylindrical body is configured to couple to said distal end of said endoscope such that said first tubular channel is in fluid communication with said second tubular channel; a plurality of elastic bands having a most proximal elastic band and a most distal elastic band, wherein each band stretched beyond its relaxed diameter and positioned around said external surface of said cylindrical body and further wherein said relaxed diameter of each band is less than the external diameter of said cylindrical body; and, a single pull line having a plurality of large beads fixed along its length, wherein said pull line has a first end and a second end and is wrapped around said external surface of said cylindrical body multiple times and under said elastic bands such that at least one bead, having a height within the range of 0.040 to 0.060 inches and a thickness within the range of 0.070 to 0.140 inches, is positioned between said elastic bands; wherein said first end of said pull line comprises a single bead and is positioned proximal to said most proximal elastic band and said second end of said pull line passes over the distal end of said cylindrical body, into said second tubular channel, through said first tubular channel, and to a retracting assembly at the proximal end of said endoscope; attaching said proximal end of said device to said distal end of said endoscope; inserting said distal end of said endoscope with attached device into a patient; maneuvering said distal end of said endoscope with attached device to a target tissue; placing said distal end of said device over said target tissue; applying suction to said proximal end of said endoscope to draw a portion of said target tissue into said device; and, actuating said retracting assembly to apply tension to said pull string to push the most distal bead set against the most distal elastic band, deploying said most distal elastic band off the distal end of said device and around said target tissue.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings.

DETAILED DESCRIPTION

Figure 1:
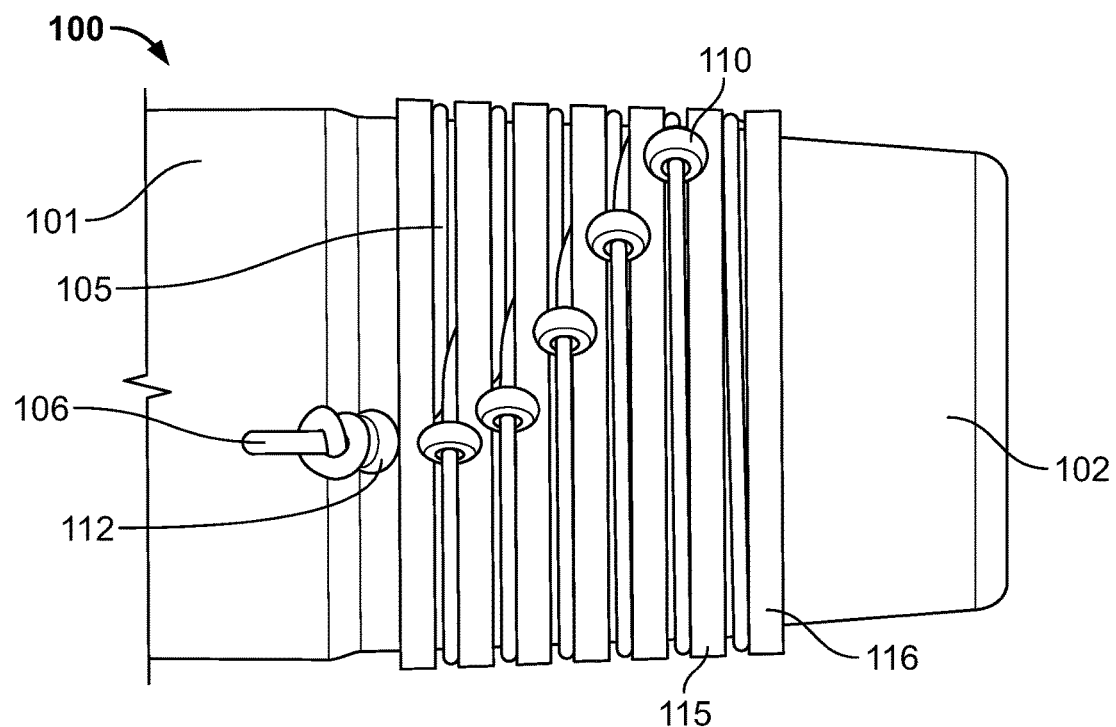
FIG. 1 is an illustration depicting a multiple band ligation device having a single string with a single bead positioned between adjacent bands, as seen in the prior art.

The present specification is directed toward a multiple band endoscopic ligation device having a single pull string and a plurality of beads positioned on said pull string and between each successive band. The device is configured to be coupled to the distal end of an endoscope and is used to deploy multiple elastic bands around target tissues to be ligated.

In one embodiment, the device of the present specification comprises a cylindrical device having a distal end and a proximal end and a tubular internal channel therebetween. In one embodiment, the proximal end of the device is sized and configured to fit snugly to the distal end of an endoscope. The device is attached to the endoscope by firmly pushing the proximal end of the device onto the distal end of the endoscope until a secure coupling is achieved. In another embodiment, the device includes connecting means at its proximal end for coupling to the distal end of the endoscope. In one embodiment, the device is tapered from its proximal end toward its distal end, such that the diameter of the device is greater at its proximal end than at its distal end. The device has a smooth external surface about which elastic ligating bands are stretched. In one embodiment, each band has squared off sides and a smooth external surface. In one embodiment, the device includes seven individual ligating bands.

The elastic bands are spaced evenly from each other and are individually encircled by a single string. The single string includes a plurality of beads fixed at specific positions along its length. In one embodiment, the beads are fixed to the string with glue. In one embodiment, the beads have an oval shape and a thin profile. In various embodiments, the beads are made of glass, hard plastic, ceramic, or any other non-compliant material. The string is looped about the outer surface of the device and between each successive band such that at least two beads are positioned between adjacent bands. In one embodiment, the string includes multiple sets of beads wherein the beads of each set are fixed in direct contact with one another.

A first end of the string terminates in a knot or any other fixing means just distal, with respect to the string, to the last set of beads. To prepare the device, the first end of the string is held on the outer surface of the device and the most proximal elastic band is stretched about and loaded onto the device and on top of the string such that the first end of the string is positioned proximally, with respect to the device, to the most proximal band. The band is placed such that the beads are positioned against the band. The most proximal elastic band is the band that is loaded first and deployed last.

The string passes under the band and continues distally along the device. The string is then wrapped around the outer surface of the device. In one embodiment, the string is wrapped one quarter turn around the device before adding the next band. The second most proximal band, with respect to the device, is then stretched and loaded onto the device and on top of the string such that at least one set of beads is positioned between the most proximal band and the second most proximal band. The string is again wrapped around the outer surface of the device and the remaining bands are loaded distally along the device in the same fashion. After the most distal band has been loaded, a second end of the string, opposite said first end, is extended around the distal end of the device, through the tubular internal channel of the device, through the endoscope body, and to a retracting assembly at the proximal end of the endoscope. In one embodiment, the retracting assembly comprises a spool configured to receive pull string slack, with attached beads, as bands are deployed. In one embodiment, the spool is attached to the proximal end of the endoscope and includes a handle whereby the operator can use the handle to spin the spool. Spinning the spool applies tension to the pull string, moving the beads distally along the device and thereby deploying bands. In various embodiments, other retracting assemblies, including but not limited to, linear mechanisms and cam mechanisms, are used to pull the string and deploy the bands.

Once attached to the distal end of an endoscope and fully loaded, the device is maneuvered by a physician to a target tissue location within a patient's body. In one embodiment, the distal end of the device is placed about the target tissue and suction is applied to the endoscope, resulting in the target tissue being drawn into the distal end of the device. The physician then uses the retracting assembly to pull the second end of the string. Tension on the second end of the string causes the beads positioned proximally to, with respect to the device, the most distal band to push the band distally along and off of the distal end of the device. The band encircles the tissue drawn into the device, effectively ligating said tissue. At this point, the physician may deploy additional bands to said tissue by further pulling on the string, or, may release the suction and move on to other target tissues to be ligated. In one embodiment, the physician can deploy up to seven ligating bands without having to reload the device.

In one embodiment, at least two beads are positioned, one directly behind the other, on each segment of string between adjacent bands and proximally, with respect to the device, the most proximal band. Having a second bead placed directly behind a first bead helps stabilize the first bead on the string by providing a thicker profile. Stabilizing the beads helps the beads to maintain geometry as they are pulled against the band, thereby preventing the band from jumping over the beads and causing a misfire.

In one embodiment, each bead set used to deploy an associated band comprises two individual beads. In another embodiment, one or more of said bead sets includes two individual beads while the remaining bead sets include only one bead. For example, in an embodiment wherein the device includes seven ligating bands, the bead sets positioned proximally, with respect to the device, the four most proximal bands, comprise two beads each while the three most distal bead sets used to deploy the three distal bands each comprise only one bead.

In another embodiment, similar bead stabilization can be achieved by using a single bead but by changing the geometry of the bead to make it larger with a thicker profile. In one embodiment, the larger, single bead has a height within a range of one and one and a half times the height of each band and a thickness within a range of one to two times the thickness of an individual bead used in a two-bead embodiment.

The present specification discloses multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the presently disclosed inventions are to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

FIG. 1 is an illustration depicting a multiple band ligating device 100 having a single string 105 with a single bead 110 positioned between adjacent bands 115, as seen in the prior art. The device 100 has a proximal end 101 and a distal end 102. The proximal end 101 is configured to attach to the distal end of an endoscope. A first end 106 of the string 105 terminates in a knot or any other fixing means just proximal, with respect to the string 105, to the last bead 112. Ligating bands 115 are deployed from the distal end 102 of the device 100 by actuating a retracting assembly which pulls on a second end of the string 105, opposite said first end, causing the bead 110 to push the most distal band 116 off the distal end of the device 100. Successive bands 115 can be deployed by further pulling on the second end of the string 105.

Conventional multiple band ligating devices encounter the problem of band misfire. As the string 105 is pulled, the band 115 can slip over the bead 110, leaving the band 115 on the device 100. Further pulling on the string 105 would most likely result in another misfire wherein another band 115 would remain on the device 100, or, would result in the undesired deployment of two bands 115 at once. Therefore, when such a misfire occurs, the device must be removed from the patient and reloaded or a new device must be attached to the endoscope.

Figure 2:
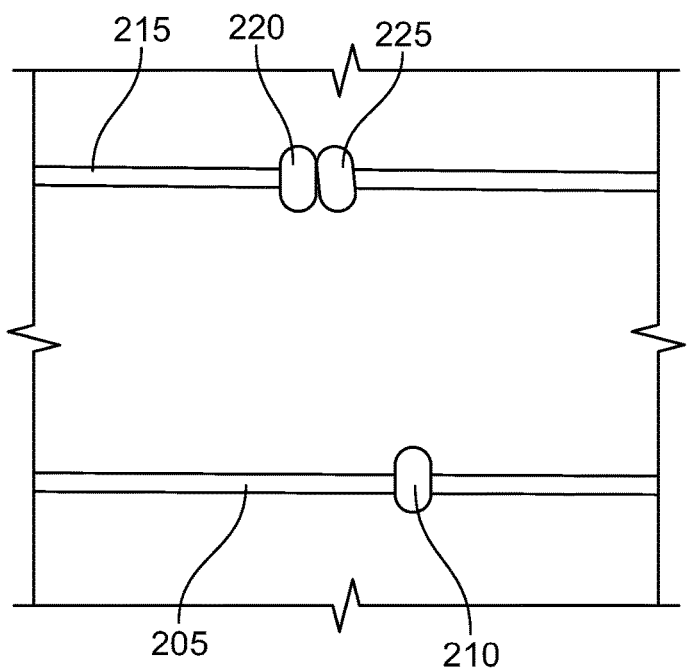
FIG. 2 is an illustration of a first pull string having a single bead positioned along its length, as seen in the prior art, and of a second pull string having two beads positioned along its length, in accordance with one embodiment of the present specification.

FIG. 2 is an illustration of a first pull string 205 having a single bead 210 positioned along its length, as seen in the prior art, and of a second pull string 215 having two beads 220, 225 positioned along its length, in accordance with one embodiment of the present specification. In the pictured embodiments, all of the beads 210, 220, 225 are oval shaped and have a thin profile. For purposes of this specification, a thin profile is defined as having a thickness no greater than 0.070 inches. As discussed above, devices using a single bead pull string 205 often encounter misfires wherein the elastic band jumps or slips over the bead and remains on the device.

In accordance with one embodiment of the present specification, the pull string 215 used to deploy bands includes two beads 220, 225 on each segment of string positioned between adjacent bands. In the pictured embodiment, a second bead 225 is positioned directly behind, and in contact with, a first bead 220. In the pictured embodiment, each of the beads 220, 225 has a thickness of 0.070 inches. In one embodiment, the beads 220, 225 are fixed to the string 215 with an adhesive. In one embodiment, the adhesive is glue. The adhesive must be placed on the string where the string and the bead meet (i.e. the bead center) and should not extend beyond the thickness of the beads. Excessive or misplaced adhesive can cause interference between the string and the bands and result in performance issues, such as band misfire. Having two beads 220, 225 positioned one directly behind the other increases the profile of the beads in comparison to the profile of one bead. The profile is increased beyond 0.070 inches but is no greater than 0.140 inches. The increased thickness or profile stabilizes the beads geometry as they are pulled against the bands and prevents the bands from slipping over the beads, thereby avoiding misfires. Having greater than two beads 220, 225 creates too large of a profile (i.e. a thickness greater than 0.140 inches) and is not advantageous for successful bead deployment.

In another embodiment (not shown), the pull string includes one single, larger bead rather than a plurality of beads along each segment between adjacent bands. The larger bead has an increased thickness and therefore an increased profile as compared to single beads used in the prior art. In one embodiment, the single, larger bead has a height within the range of 0.040 and 0.060 inches and a thickness within the range of 0.070 and 0.140 inches. Having a larger profile helps to maintain bead geometry, thereby stabilizing the bead as it is pulled against the band and preventing the band from slipping over the bead.

Figure 3A:
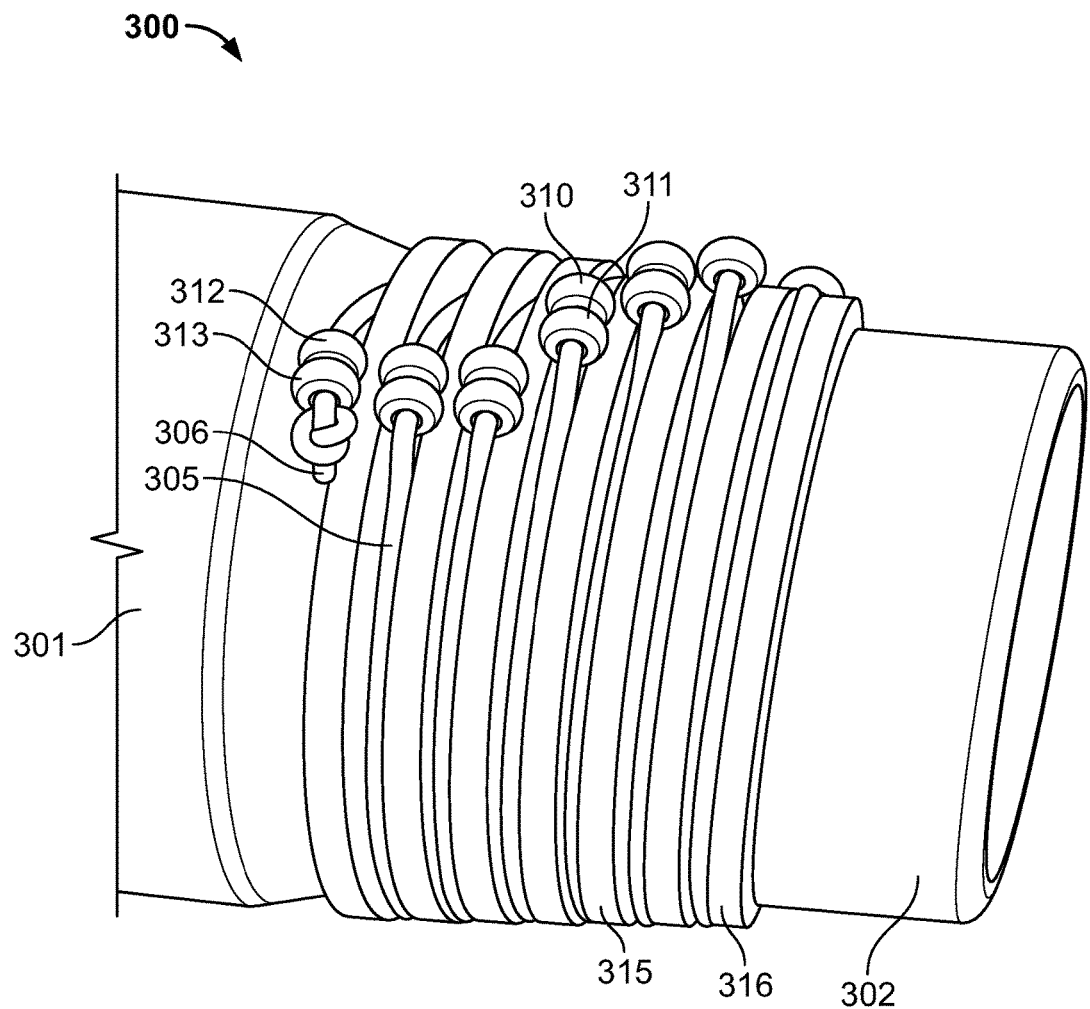
FIG. 3A is an illustration depicting a multiple band ligation device having a single string with two beads positioned between adjacent bands, in accordance with one embodiment of the present specification.

FIG. 3A is an illustration depicting a multiple band ligation device 300 having a single string 305 with two beads 310, 311 positioned between adjacent bands 315, in accordance with one embodiment of the present specification. In one embodiment, each bead measures between 0.040 and 0.060 inches in height and has a thickness between 0.050 and 0.090 inches. In one embodiment, each bead has a thickness of 0.070 inches. In one embodiment, each band has a height of 0.040 inches. The device 300 is attached at its proximal end 301 to the distal end of an endoscope. A first end 306 of the string 305 terminates in a knot or any other fixing means just proximal, with respect to the string 305, to the last pair of beads 312, 313. Ligating bands 315 are deployed from the distal end 302 of the device 300 by actuating a retracting assembly which pulls on a second end of the string 305, opposite said first end, causing the beads 310, 311 to push the most distal band 316 off the distal end of the device 300. Successive bands 315 can be deployed by further pulling on the second end of the string 305.

Figure 3B:
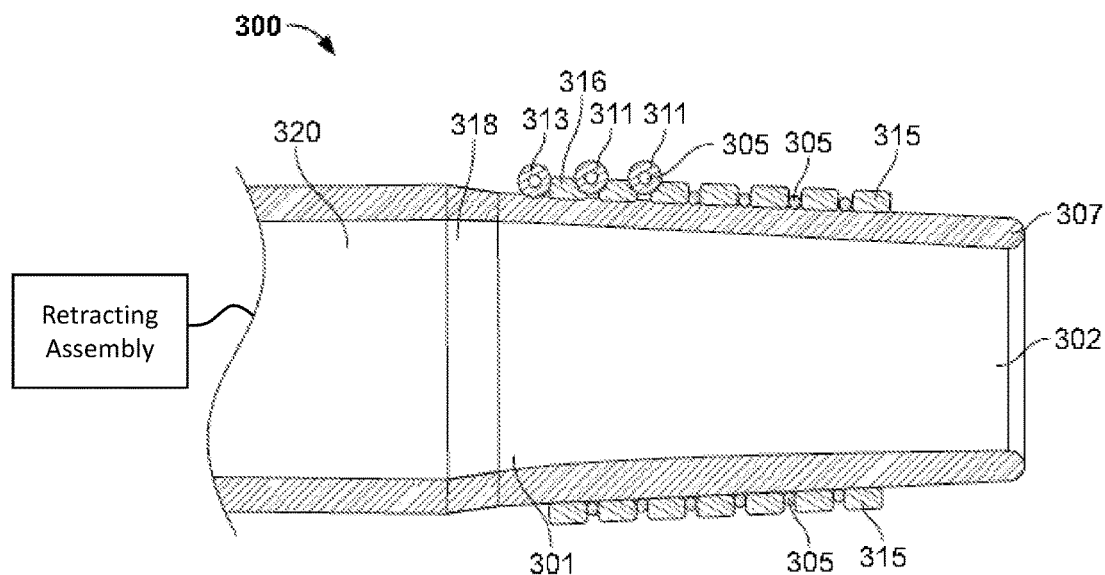
FIG. 3B is a side view cross sectional illustration of the multiple band ligation device of FIG. 3A.

FIG. 3B is a side view cross sectional illustration of the multiple band ligation device 300 of FIG. 3A. In the pictured embodiment, the device 300 includes seven bands 315, 316 stretched out and placed on the device body 307. Segments of pull string 305 can be seen wrapped around the device body 307 between adjacent bands 315. Bead 313 of the most proximal, with respect to the device 300, bead set is positioned proximally to the most proximal band 316. Also depicted are beads 311 of the second most and third most proximal, with respect to the device 300, bead sets. The pull string 305 passes through the center of each bead 311, 313. Additional bead sets are positioned between the remaining adjacent bands 315 but are offset from those discussed and as such are not pictured in this view.

The distal end 302 of the device 300 comprises an opening for placement over the target tissue. In one embodiment, the proximal end 301 of the device is sized and configured to fit snugly over the distal end of an endoscope 320. In another embodiment, the proximal end 301 of the device 300 includes a means 318 for coupling the proximal end 301 of the device 300 to the distal end of the endoscope 320. In one embodiment, the coupling means 318 includes a flexible adapter that fits over the distal end of the endoscope and is fixed to the proximal end 301 of the device 300.

Figure 3C:
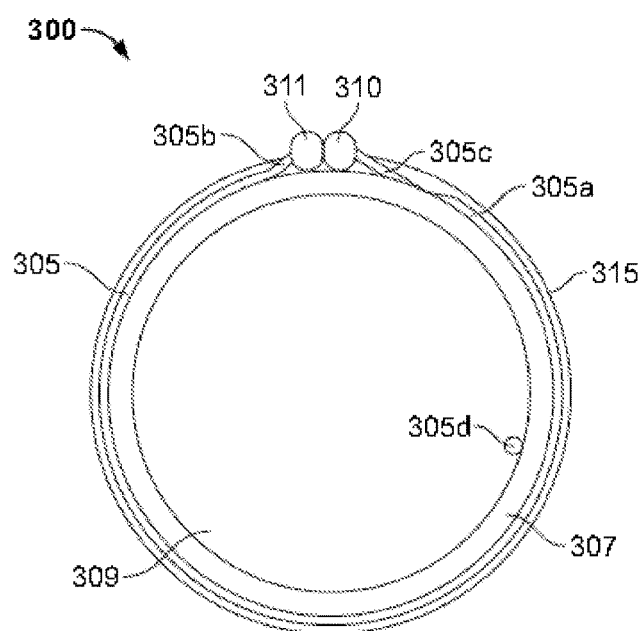
FIG. 3C is a front view cross sectional illustration of the multiple band ligation device of FIG. 3A; and, FIG. 4 is a flow chart illustrating the steps involved in the deployment of ligating bands using an exemplary embodiment of the device of the present specification.

FIG. 3C is a front view cross sectional illustration of the multiple band ligation device 300 of FIG. 3A. As discussed, the device 300 comprises a cylindrical body 307 with a hollow center channel 309. A single pull string 305 and seven bands 315 are wrapped about the device 300. The pull string 305 includes a plurality of bead sets along its length. FIG. 3C represents a cross sectional slice through the cylindrical body 307, the pull string 305, and a pair of beads 310, 311 of one bead set when viewed from the front. As such, for purposes of the illustration, the distal end of the device 300 would extend outward from the plane of the figure and toward the reader and the proximal end of the device would extend inward from the plane of the figure and away from the reader.

Point 305a represents the position where the pull string 305 emerges from under the next most proximal band 315. The pull string 305 is wrapped tightly around the outer surface of the cylindrical body 307 until it reaches the bead set 310, 311. At point 305b, the pull string 305 is lifted slightly off the cylindrical body 307 and passes through the center of the beads 310, 311. The pull string 305 is fixed to the beads 310, 311 where it passes through the beads 310, 311 centers. At point 305c, after emerging from bead 310, the pull string 305 extends distally along the device 300 and under the next most distal band (not shown). The pull string continues in the same manner distally around the cylindrical body 307 and under each remaining band with a bead set between adjacent bands. After passing under the most distal band, the pull string 305 wraps over the distal end of the cylindrical body 307 and extends proximally through the device center channel 309, as depicted at point 305d. The pull string 305 continues proximally through the center channel of the endoscope to a retracting assembly at the proximal end of the endoscope.

Figure 4:
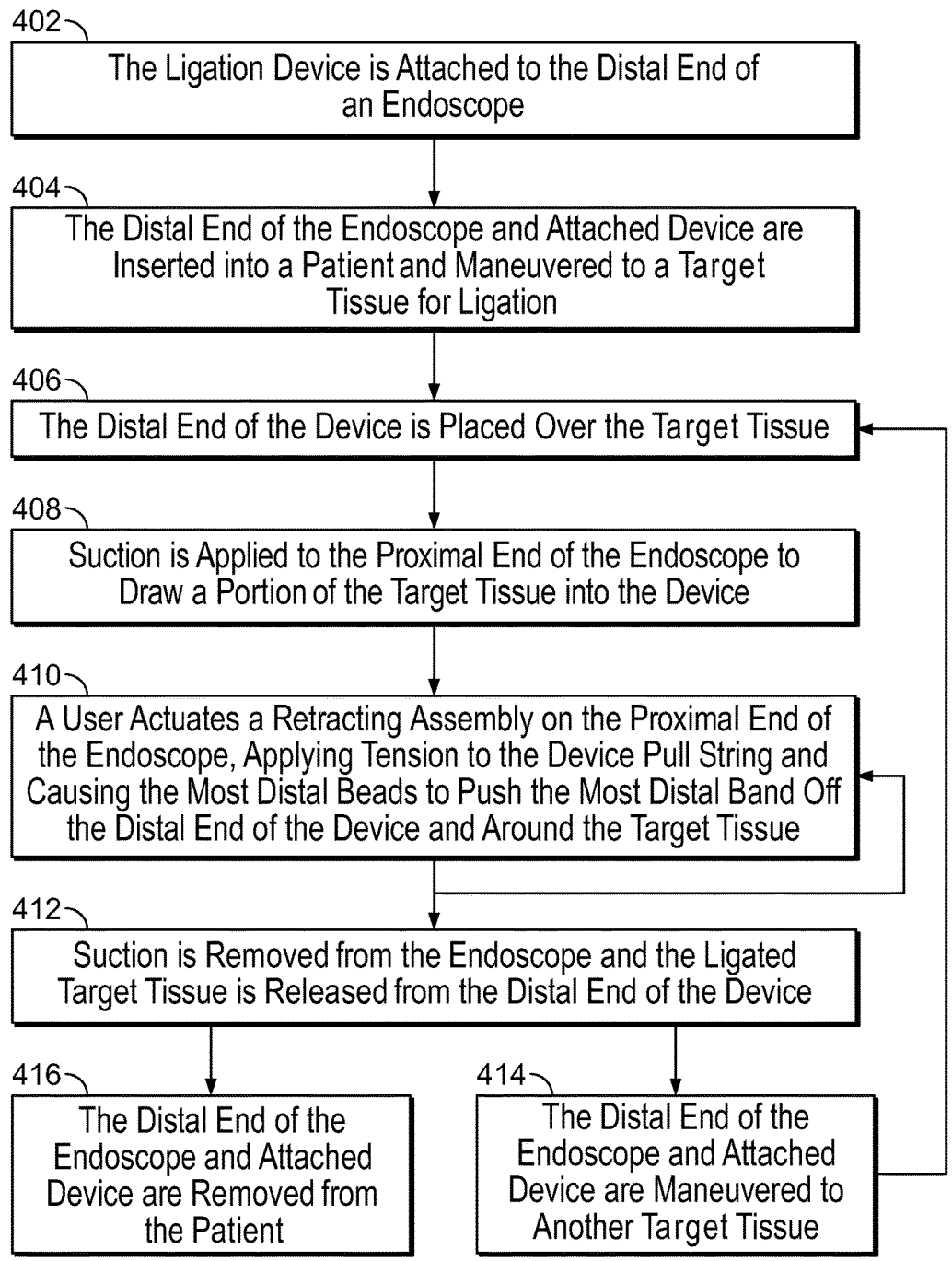

FIG. 4 is a flow chart illustrating the steps involved in the deployment of ligating bands using an exemplary embodiment of the device of the present specification. At step 402, a multiple band endoscopic ligation device as described in the present specification is attached to the distal end of an endoscope. The distal end of the endoscope and the attached device are then inserted into a patient and maneuvered to a target tissue at step 404. At step 406, the distal end of the device is placed over the tissue to be ligated. Suction is applied to the proximal end of the endoscope at step 408 to draw a portion of the target tissue into the device. Then, at step 410, a user actuates a retracting assembly on the proximal end of the endoscope which results in tension being applied to the device's pull string. Tension on the pull string causes the most distal beads to push the most distal band off of the distal end of the device and around the target tissue. If the physician wishes to apply more ligating bands to the target tissue, then the deployment procedure of step 410 is repeated.

Suction is then removed from the endoscope and the ligated target tissue is released from the distal end of the device at step 412. If there are more target tissues within the patient and the device still has bands available, then the distal end of the endoscope and the attached device are maneuvered to another target tissue at step 414. The user then repeats steps 406 through 412 to ligate the remaining target tissues. Once no other tissues remain to be ligated, the distal end of the endoscope and the attached device are removed from the patient at step 416.

Exemplary Case Study

A multiple band endoscopic ligation device with a single pull string having only one bead to deploy each band, as seen in the prior art, was tested against a multiple band endoscopic ligation device with a single pull string having two beads to deploy each band, in accordance with one embodiment of the present specification. Each device comprised six bands and the rate of successful band deployment for each band was measured for both devices. Table 1 lists the successful band deployment rates for the two devices.

TABLE 1

Successful Band Deployment Rates

| Device having one bead for deployment | | Device having two beads for deployment | |
| --- | --- | --- | --- |
| Band Number (Most Distal on Device First) | Success Rate (95% Confidence Interval) | Band Number (Most Distal on Device First) | Success Rate (95% Confidence Interval) |
| First Band | 91% | First Band | 91% |
| Second Band | 91% | Second Band | 91% |
| Third Band | 91% | Third Band | 91% |
| Fourth Band | 85% | Fourth Band | 91% |
| Fifth Band | 85% | Fifth Band | 91% |
| Sixth Band | 76% | Sixth Band | 91% |

As can be seen in Table 1, the two devices had the same success rate, 91% at the 95% confidence interval, for the first three, or most distal three, with respect to the device, ligation bands. However, starting with the fourth most distal band, the success rate for the single bead device began to decline, dropping to 85%, signifying more misfires, while the success rate for the two bead device remained at 91% at the 95% confidence interval. The success rates for the fifth band were again 85% and 91% for the single bead device and two bead device, respectively. The single bead device encountered the highest rate of failure with the sixth band, having only a 76% successful deployment rate at the 95% confidence interval while the success rate for the two bead device again remained at 91%. Hence, the use of a pull string with two beads for pushing bands off the device increases the likelihood of successful band deployment over a device using a pull string with only one bead, particularly with respect to the bands positioned more proximally on the device. To achieve the same success rates, one can have an embodiment with the first three bands having associated therewith a single bead and the next three bands having associated therewith two beads. Alternatively, some subset of the bands can have a single bead while the remainder can have two beads.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

I claim:

1. A method for ligating internal body tissues, said method comprising the steps of:
   providing an endoscopic ligation device for use with an endoscope having a proximal end and a distal end and a first tubular channel therebetween, said device comprising:
      a cylindrical body having a smooth external surface, a diameter, a proximal end and a distal end and a second tubular channel therebetween wherein said proximal end of said cylindrical body is configured to couple to said distal end of said endoscope;
      a plurality of elastic bands having a most proximal elastic band and a most distal elastic band, wherein each band stretched beyond its relaxed diameter and positioned around said external surface of said cylindrical body and further wherein said relaxed diameter of each band is less than the external diameter of said cylindrical body; and,
      a single pull line having a plurality of bead sets fixed along its length, wherein each of said bead sets comprises at least two beads positioned one directly in contact with the other, further wherein said pull line has a first end and a second end and is wrapped around said external surface of said cylindrical body multiple times and under said elastic bands such that at least one set of beads is positioned between said elastic bands;
   wherein said first end of said pull line comprises a bead set and is positioned proximal to said most proximal elastic band and said second end of said pull line is attached to a retracting assembly at the proximal end of said endoscope;
   attaching said proximal end of said device to said distal end of said endoscope;
   inserting said distal end of said endoscope with attached device into a patient;
   maneuvering said distal end of said endoscope with attached device to a target tissue;
   placing said distal end of said device over said target tissue;
   applying suction to said proximal end of said endoscope to draw a portion of said target tissue into said device; and,
   actuating said retracting assembly to apply tension to said pull string to push a most distal bead set against a most distal elastic band, deploying said most distal elastic band off the distal end of said device and around said target tissue.

2. The method for ligating internal body tissues of claim 1, wherein said proximal end of said cylindrical body is configured to couple to said distal end of said endoscope such that said first tubular channel is in fluid communication with said second tubular channel.

3. The method for ligating internal body tissues of claim 2, wherein said first end of said pull line comprises a bead set and is positioned proximal to said most proximal elastic band and said second end of said pull line passes over the distal end of said cylindrical body, into said second tubular channel, through said first tubular channel, and to the retracting assembly at the proximal end of said endoscope.

4. The method for ligating internal body tissues of claim 1, wherein said retracting assembly comprises any one of a spooling mechanism, a linear mechanism, and a cam mechanism.

5. The method for ligating internal body tissues of claim 1, wherein said cylindrical body has a first diameter at said proximal end and a second diameter at said distal end wherein said first diameter is greater than said second diameter and wherein said first and second diameters are greater than said relaxed diameter of said elastic bands.

6. The method for ligating internal body tissues of claim 1, wherein said beads are made of a material and wherein said material comprises at least one of glass, hard plastic, and ceramic.

7. The method for ligating internal body tissues of claim 1, wherein each of said beads measures between 0.040 and 0.060 inches in height and has a thickness of between 0.050 and 0.090 inches.

8. The method for ligating internal body tissues of claim 1, wherein each of said plurality of elastic bands has a height of approximately 0.040 inches.

9. The method for ligating internal body tissues of claim 1, wherein said beads are fixed to said pull line with glue.

10. The method for ligating internal body tissues of claim 1 wherein said plurality of elastic bands equals seven.

11. The method for ligating internal body tissues of claim 1 wherein said pull line passes one quarter length around the outer surface of said cylindrical body between each set of bands.

12. The method for ligating internal body tissues of claim 1 further comprising a flexible adapter configured to fit over the distal end of the endoscope, wherein said proximal end of said cylindrical body attaches the flexible adapter in order couple to said distal end of said endoscope.

13. The method for ligating internal body tissues of claim 1 further comprising:
   maneuvering said distal end of said endoscope with attached device to a second target tissue;
   placing said distal end of said device over said second target tissue;
   applying suction to said proximal end of said endoscope to draw a portion of said second target tissue into said device; and,
   actuating said retracting assembly to apply tension to said pull string to push a second most distal bead set against a second most distal elastic band, deploying said second most distal elastic band off the distal end of said device and around said second target tissue.

14. The method for ligating internal body tissues of claim 1 wherein a success rate for deploying said most distal elastic band is equal to a success rate for deploying a most proximal elastic band.

15. The method for ligating internal body tissues of claim 1 wherein a success rate for deploying a most distal elastic band is equal to a success rate for deploying a second most proximal elastic band.

16. The method for ligating internal body tissues of claim 1 wherein a success rate for deploying a second most distal elastic band is equal to a success rate for deploying a most proximal elastic band.

17. The method for ligating internal body tissues of claim 1 wherein a success rate for deploying a second most distal elastic band is equal to a success rate for deploying a second most proximal elastic band.

18. The method for ligating internal body tissues of claim 1 wherein a deployment success rate is equal for all elastic bands.

* * * * *